(12) United States Patent
Psakhie et al.

(10) Patent No.: US 10,105,318 B2
(45) Date of Patent: Oct. 23, 2018

(54) LOW-DIMENSIONAL STRUCTURES OF ORGANIC AND/OR INORGANIC SUBSTANCES AND USE THEREOF

(71) Applicants: Institute of Strength Physics and Materials Science of Siberian Branch Russian Academy of Sciences (ISPMS SB RAS), Tomsk (RU); Jozef Stefan Institute, Ljubljana (SI); National Research Tomsk Polytechnic University (TPU), Tomsk (RU)

(72) Inventors: Sergey G. Psakhie, Tomsk (RU); Marat I. Lerner, Tomsk (RU); Elena A. Glazkova, Tomsk (RU); Olga V. Bakina, Tomsk (RU); Olga Vasiljeva, Domzale (SI); Georgy A. Mikhaylov, Ljubljana (SI); Boris Turk, Skofljica (SI)

(73) Assignees: Institute of Strength Physics and Materials Science of Siberian Branch Russian Academy of Sciences (ISPMS SB RAS), Tomsk (RU); Jozef Stefan Institute, Ljubljana (SI); National Research Tomsk Polytechnic University (TPU), Tomsk (RU)

( * ) Notice: Subject to any disclaimer, the term of this patent is extended or adjusted under 35 U.S.C. 154(b) by 242 days.

(21) Appl. No.: 14/945,987

(22) Filed: Nov. 19, 2015

(65) Prior Publication Data
US 2016/0074325 A1    Mar. 17, 2016

Related U.S. Application Data

(63) Continuation of application No. PCT/RU2014/000354, filed on May 19, 2014.

(30) Foreign Application Priority Data

May 20, 2013    (RU) ................................ 2013123074

(51) Int. Cl.
  *A61K 9/16*    (2006.01)
  *A61L 15/18*    (2006.01)
  (Continued)

(52) U.S. Cl.
  CPC ................ *A61K 9/16* (2013.01); *A61K 33/08* (2013.01); *A61K 33/24* (2013.01); *A61K 33/26* (2013.01);
  (Continued)

(58) Field of Classification Search
  CPC ........ A61K 33/08; A61K 33/24; A61K 33/26; A61K 9/16; A61K 9/1611; A61K 9/1635;
  (Continued)

(56) References Cited

U.S. PATENT DOCUMENTS 5,229,200 A * 7/1993 Sassa ................ A41D 31/0072
                                                                210/243
8,033,400 B2    10/2011 Lerner et al.
(Continued)

FOREIGN PATENT DOCUMENTS

RU        2253903 C2    6/2005
RU        2270663 C2    2/2006
(Continued)

OTHER PUBLICATIONS

International Search Report from PCT/RU2014/000354, filed May 19, 2014, dated Sep. 25, 2014.
(Continued)

*Primary Examiner* — Ernst V Arnold
(74) *Attorney, Agent, or Firm* — Patentbar International, P.C.

(57) ABSTRACT

The object of the present invention is low-dimensional, primarily 2D folded structures of organic and/or inorganic substances and/or their agglomerates, which have folds and faces of irregular shape and exhibit high local electric field strength generated by surface charges on the said folds, faces
(Continued)

and edges, and use thereof: as sorbents of organic particles (molecules, bacteria, viruses, proteins, antigens, endotoxins) and inorganic particles (metal ions, colloids); as an agent with wound healing and antibacterial activity; as an agent for tumor cell growth inhibition.

14 Claims, 10 Drawing Sheets

(51) Int. Cl.
  *B01J 20/06* (2006.01)
  *A61K 33/08* (2006.01)
  *A61K 33/24* (2006.01)
  *A61K 33/26* (2006.01)
  *A61L 27/20* (2006.01)
  *A61L 27/50* (2006.01)
  *A61L 15/28* (2006.01)
  *A61L 15/42* (2006.01)
  *B01J 20/28* (2006.01)
  *B01J 20/24* (2006.01)
  *B01J 20/26* (2006.01)
  *B01J 20/08* (2006.01)

(52) U.S. Cl.
  CPC ............... *A61L 15/18* (2013.01); *A61L 15/28* (2013.01); *A61L 15/42* (2013.01); *A61L 27/20* (2013.01); *A61L 27/50* (2013.01); *B01J 20/06* (2013.01); *B01J 20/08* (2013.01); *B01J 20/24* (2013.01); *B01J 20/261* (2013.01); *B01J 20/28014* (2013.01); *A61K 9/1611* (2013.01); *A61K 9/1635* (2013.01)

(58) Field of Classification Search
  CPC .......... A61L 15/18; A61L 15/28; A61L 15/42; A61L 27/20; A61L 27/50; B01J 20/06; B01J 20/08; B01J 20/24; B01J 20/261; B01J 20/28014
  See application file for complete search history.

(56) References Cited

U.S. PATENT DOCUMENTS

| | | | |
|---|---|---|---|
| 2002/0197296 A1* | 12/2002 | Gen | A61L 2/081 424/423 |
| 2010/0003203 A1* | 1/2010 | Karpov | B82Y 30/00 424/59 |

FOREIGN PATENT DOCUMENTS

| | | |
|---|---|---|
| RU | 2304463 C2 | 8/2007 |
| RU | 2313387 C2 | 12/2007 |
| RU | 2317843 C2 | 2/2008 |
| RU | 2321898 C1 | 4/2008 |
| RU | 2328447 C1 | 7/2008 |
| RU | 2397781 C1 | 8/2010 |
| RU | 2398628 C2 | 9/2010 |
| RU | 2426557 C1 | 8/2011 |
| RU | 2466713 C1 | 11/2012 |
| RU | 2468129 C2 | 11/2012 |
| RU | 2011116705 A | 11/2012 |
| RU | 2471349 C2 | 1/2013 |
| WO | 2006032727 A1 | 3/2006 |

OTHER PUBLICATIONS

Reid B. et al., Wound Healing in Rat Cornea: The Role of Electric Currents, The FASEB Journal, Mar. 2005, pp. 379-386, vol. 19.
Keese C.R., et al, Electrical Wound-Healing Assay for Cells in Vitro, Proc. Natl Acad. Sci. USA, Feb. 10, 2004, pp. 1554-1559, vol. 101, No. 6.
Binggeli R. et al., Cellular Potentials of Normal and Cancerous Fibroblasts and Hepatocytes, Cancer Research, Jun. 1980, pp. 1830-1835, vol. 40.
Sundelacruz S. et al, Role of Membrane Potential in the Regulation of Cell. Proliferation and Differentiation, Stem Cell Rev. and Rep., 2009, pp. 231-246, vol. 5.
Fantin V.R. et al, A Novel Mitochondriotoxic Small Molecule that Selectively Inhibits Tumor Cell Growth, Cancer Cell, Jul. 2002, pp. 29-42, vol. 2.
Steve Haltiwanger M.D., The Electrical Properties of Cancer Cells, http://www.royalrife.com/haltiwanger1.pdf.
SanPiN 2.1.4.1074-01 Drinking Water. Hygienic Requirements on Water Quality in Drinking Water Supply Systems. Quality Control.
Zhao M., et al, Electrical Signals Control Wound Healing through Phosphatidylinositol-3-OH Kinase-y and PTEN, Nature Letters, Jul. 27, 2006, pp. 457-460, vol. 442.
Cone Jr., C. D., Unified Theory on the Basic Mechanism of Normal Mitotic Control and Oncogenesis, Journal of Theoretical Biology, 1971, pp. 151-181, vol. 30.
Marino A.A., et al., Association between Cell Membrane Potential and Breast Cancer, Tumor Biology, 1994, pp. 82-89, vol. 15.
Larichev M.N., et al, Production of Nonstructured Products in Micron-Sized Aluminum Powder Oxidation by Water in Ultrasonic Field, Scientific session of MEPhI-2010, v.2 Nanophysics and nanotechnology. Fundamental problems of science, p. 141, http://new.library.mephi.ru/934/elbib/izdvuza/scientific-sessions?Year=2010&Volume=1.
Drobyshev V.A., Polymedel: Medical Application of Polymer Electret Film Polymedel, Novosibirsk: IPK Chuvashiya, 2010, p. 1-36.
Savelyev I.V., Physics, a General Course, Moscow: Mir, 1981, pp. 17-19.
Gorokhovatskii Yu.A., The Electret Effect and Its Application, Soros Educational Journal, 1997, No. 8, pp. 92-98.
Tepper, Fred and Kaledin, Leonid, Virus and Protein Separation Using Nano Alumina Fiber Media, Argonide Corporation, Sanford, Florida, http://www.nanoceram.com/LinkClick.aspx?fileticket=3n6HTUFMUg%3D&tabid=57&mid=377.
Voroshilova A. A. et al, Oil-Oxidizing Bacteria as Markers of Biological Oil Oxidation Intensity under Natural Conditions, Microbiologiya, 1952, pp. 408-415, vol. 21, No. 4.
Bakina O. V. et al. Behavior of Alyuminum Nitride Composite Nanopowders in Aqueous Media, Fundamental Research, Chemical Sciences, 2013, No. 4, pp. 862-867.
European Convention for the Protection of Vertebrate Animals used for Experimental and other Scientific Purposes (Strasbourg, 18.III.1986).
Lozhkomoev A. S., Adsorptive capacity of the nanostructured aluminum oxyhydroxide immobilized on the cellulose acetate microfibers, Abstract of the thesis for the scientific degree of candidate of chemical sciences, Tomsk 2009.

* cited by examiner

LOW-DIMENSIONAL STRUCTURES OF ORGANIC AND/OR INORGANIC SUBSTANCES AND USE THEREOF

RELATED APPLICATIONS

This Application is a Continuation application of International Application PCT/RU2014/000354, filed on May 19, 2014, which in turn claims priority to Russian Patent Applications No. RU2013123074, filed May 20, 2013, both of which are incorporated herein by reference in their entirety.

FIELD OF INVENTION

The invention relates to low-dimensional structures of organic and/or inorganic substances, primarily 2D folded structures and their agglomerates, which are able to act selectively on living cells and can be used in medicine and pharmacy for cancer cell inhibition.

BACKGROUND OF THE INVENTION

It is known that epithelial layer damage causes transepithelial difference of potentials [1, 2], an increase in endogenous electric fields of the wound and, as a result, accelerated wound healing. An increase in the electric field strength induced by a cathode applied to the wound increases the rate of epithelium motion to the wound [3].

Additionally, the association between the cell membrane potential and cancer was observed in many studies performed for normal and transformed cell lines.

Cone [4] suggested based on these data that the transmembrane potential can control the mitotic cycle. The main idea is that a decrease in the membrane potential initiates the cell cycle. He explains oncogenesis assuming that the cell after mitosis loses the capability to restore its normal electronegative cell membrane potential and, consequently, has to repeat the cell cycle. Later this assumption was confirmed by different authors. For example, Marino et al. [5] showed that the average cell membrane potential of breast with infiltrating ductal carcinoma was highly depolarized compared to the values measured in tissues with breast benign disease. Depolarization was also observed in transformed epithelial breast cells compared to normal breast cells.

Binggeli et al. [6] revealed differences in the electrical properties of normal and cancer cells. Comparison of the membrane potential of normal and transformed cells showed that cancer cells (sarcomas) have lower negative potential (e.g., the normal cell potential is 42.5±5.4 mV, and cancer cell potential is 14.3±5.4 mV).

Sundelacruz et al. [7] showed that by regulating the cell membrane potential, as well as that of cancer cells, it is possible to control their proliferation and differentiation.

It is known that nano- and microstructured hydroxides and oxyhydroxides are used in various materials and technological processes, in biology and medicine.

There is a method of producing an improved fibrous filtering material [RU 2011116705 A, publ. 10 Nov. 2012] wherein an aluminum and silicon oxyhydroxide layer with positive surface charge is formed on the surface of a fibrous material, for which an $Al_2O_3$—$SiO_2$ solution is prepared and deposited on a fibrous ceramic material.

Disadvantages of this method are that the positive surface charge is generated based on the known properties of structured silicon whose coatings are formed in treatment of the fibrous ceramic material.

There is a one-nanometer positive fiber adsorbent, described in [RU 2304463 C2, publ. 20 Aug. 2007], which consists of non-spherical aluminum oxyhydroxide particles shaped as fibers of diameter less than 50 nm and having the length to thickness ratio of more than five to one. The adsorbent is produced in a reaction of interaction between initial aluminum component and water solution at a temperature of up to 100° C. and applied directly to the fiber surface. It has a capability to adsorb at least one electronegative particle from the liquid.

There is a method of producing nanofibers of oxide-hydroxide phases with boehmite structure [RU 2328447 C1, publ. 10 Jul. 2008] which can be applied to produce adsorbents for fine purification of drinking water, industrial and waste water. The nanofibers of aluminum oxide-hydroxide phases are produced by hydrolysis of powder synthesized by electrical explosion of aluminum wire of diameter $0.3 < d \leq 0.4$ mm in nitrogen atmosphere under pressure $P < 3$ atm and energy $19.8\ J/mm^3 < E \leq 66\ J/mm^3$ applied to the wire. Subsequent powder hydrolysis is carried out at a temperature of more than 70° C. The produced nanofibers of aluminum oxide-hydroxide phases have the length 0.1-0.2 μm, diameter 0.001-0.013 μm and specific surface area up to 500 $m^2/g$.

Patent [U.S. Pat. No. 8,033,400 B2, publ. 11 Oct. 2011] discloses a filtering material produced on the basis of nonwoven organic synthetic polymeric fabric and positively charged agglomerates of aluminum hydroxide nanofibers. Patent [RU 2397781 C1, publ. 27 Aug. 2010] discloses a nonwoven material for medical purposes which has wound healing, antibacterial and antiviral activity, and wound dressings on its basis made of a fibrous material with highly porous alumina hydrate particles fixed on its fibers.

A disadvantage of the known nanosized fibrous adsorbents described in [RU2304463 C2 and RU 2328447 C1, RU 2397781 C1, U.S. Pat. No. 8,033,400 B2] are a relatively low sorption capacity due to the shape and arrangement of fibers or nanofibers. This is confirmed by the data provided by Tepper and Kaledin in the paper "Virus and Protein Separation Using Nano Alumina Fiber Media" [http://www.argonide.com/publications/laboratory.pdf]. The paper contains micrographs of nanofibers that form close-packed structures. As a result, the pore space of the sorption nanofibrous material is less accessible to the sorbate (bacteria, colloidal particles, etc.) than the pore space of agglomerates of low-dimensional folded structures. The micrographs demonstrate that colloidal particles are primarily adsorbed to nanofiber ends, rather than between nanofibers. Consequently, nanofibers with large specific surface area have low sorption capacity.

Larichev et al. [8] studied the hydrolysis of commercial aluminum powder of grade ASD-4 with an average grain size of about 4 μm produced in Russia. The authors investigated aluminum oxidation in distilled water and in the $Ca(OH)_2$ saturated aqueous solution (buffer activator) with and without ultrasonic field application. The degree of ASD-4 oxidation in distilled water for a reasonable time (a few days) without an ultrasonic field does not exceed 30%. A cellular structure of oxidation products is formed on the surface of the initial aluminum particles. A combination of ultrasonic and buffer activation considerably changes the process, the oxidation degree increases to 100%. In this case, rod-shaped nanostructures are formed. The BET surface area of such products is only 40 $m^2/g$.

The aforementioned rod-shaped nanostructures have small specific surface area and hence their sorption properties might be low. No data are provided on whether these nanofibers can generate an electric field in aqueous media.

There is a process for the preparation of an adsorbent containing iron oxyhydroxide FeO(OH), adsorbent material and use thereof, described in [WO2006032727 (A1), publ. 2006 Mar. 30]. The invention relates to a process for producing an adsorbent material that contains iron oxyhydroxide, wherein an iron oxyhydroxide mass with a moisture content of 5-15 wt % is produced, the mass is granulated by compaction, followed by comminution and sieving of the compacted product to give product granules of grain size ranging from 0.5 to 4 mm.

The disclosed adsorbent represents granules of size ranging from 0.5 to 4.0 mm Granules of this size would not generate a high-strength electric field which is necessary for effective adsorption of charged particles and for the effect on cell membranes.

There is a method of producing biopreparation ferrigel [RU 2466713, publ. 20 Nov. 2012] on the basis of nanosized ferric oxyhydroxide. The biopreparation is produced by mixing ferric oxyhydroxide recovered at underwater deferrization stations with water soluble polymer and glycerol.

The patent description provides no information on the shape of the ferric oxyhydroxide particles and on the properties responsible for their biological activity, such as accelerated wound healing. Moreover, the ferric oxyhydroxide particles mixed with water soluble polymers and glycerol would be coated with these substances and hence a larger part of their surface would be inaccessible for biological objects.

There are polymer materials for wound healing and cancer cell inhibition.

Patent [RU 2471349, publ. 10 Jan. 2013] discloses a polymer material for elimination of live target cells. The material contains at least one insoluble hydrophobic anionic, cationic or amphoteric charged polymer. The polymer in contact with water-containing environment:
  a) is a carrier of strongly acidic or strongly basic functional groups;
  b) has a pH value lower than 4.5 or higher than 8.0; and
  c) possesses proton conductivity and/or electrical potential sufficient for the disruption of pH homeostasis and/or electrical balance inside the closed cell volume.

The charged polymer preserves the pH value of the medium, changing the pH value only within the cell. The shift of the aqueous medium pH to the acidic (pH less than 4.5) or alkaline range (pH higher than 8.0) induces cell death in prokaryotes and eukaryotes. The said material can be regenerated by the regeneration of charged polymer, buffer capacity and proton conductivity of the material.

The suggested cell death mechanism associated with pH and/or electric balance change in the cell volume is in doubt. This mechanism has no evidential basis because modern science and technology do not permit the measurement of pH and/or electric balance within the cell. The data and examples provided in the patent indicate that cell death induces a local pH change in the aqueous medium surrounding the cell; pH of the entire medium can remain unchanged due to low concentration of the active material. According to the disclosure, the object of the invention is to produce materials (insoluble proton reservoirs or sources) containing easily dissociated cationic and/or anionic groups spatially arranged so that to effectively minimize pH change in a medium" i.e. a minimum pH change of the medium was observed. As is known from chemistry, when a substance disassociates into ions, they inevitably appear in the medium.

Cells are thus affected due to the formation of conditions on the cell surface or in the vicinity of cells (high or low pH values) under which both cancer and normal cells cannot live. The use of such materials for the treatment of oncological patients or for the application as an antimicrobial agent is therefore greatly restricted.

There is a polymer electret healing film (applicator) Polymedel [9]. The electrets used in surgery activate reparative processes in chronic nonhealing wounds, pressure ulcers, neurotrophic ulcers and thermal injuries. The rate of necrotic tissue reduction in the wound decreases significantly, substantial wound granulation is accelerated, epithelization of wound edges begins earlier, transition of the process from the second to the third stage (damage through entire skin) and from the third to the fourth stage (destruction of skin and underlying tissue) is inhibited or even stops. Recent studies showed that an electret applied to various painful regions reduces pain (arthritis, osteochondrosis, radiculitis, bruises, renal colics and so on). An applied electric field causes microvibration and microconvection within a biological tissue which are induced by electrohydrodynamic forces. This changes the rate of metabolic processes, cell permeability, the rate of reagent delivery to membrane surfaces and macromolecules.

Disadvantages of electret films are that cells are affected indirectly, via microvibration and microconvection arising within biological tissue under the action of electrohydrodynamic forces. There is no direct influence on the cell membrane potential. Consequently, the electret film efficiency is low. The application of polymer electret film on wounds with heavy or purulent drainage would reduce air flow to the wound, which is inadmissible and can make a disease worse. There is also no documented evidence on oncological diseases cured with the use of electret materials.

There are physical methods of cancer cell treatment using an electric field.

There is a method for treating pathological proliferation of body cells [RU 2270663 C2, publ. 27 Feb. 2006] wherein biologically active points are chosen and treated. A biologically active point corresponding to an organ with pathological cell proliferation is chosen and the potential of the chosen point is measured with respect to a reference point. Then, an external source of direct electric field is attached to the chosen points. The poles of this source should be opposite in sign to the poles of the points, and its absolute value should be equal to the difference of the absolute values of the measured potential and the potential corresponding to the healthy organ in the chosen point. The electric field is applied until the cancer cell membrane potential reaches the membrane potential of the healthy organ. As a result, biochemical processes in cells are normalized, due to which the pathological activity of cancer cells is significantly reduced and, in the limiting case, cells recover their normal state.

There is a method of stopping carcinoma cell division [RU2253903, publ. 10 Jun. 2005] based on exposing a cell or a group of cells to an external energy source, wherein at least two electrodes are applied before treating the cells. One of the electrodes is attached to the cytoplasmatic side of the cell membrane and the other is attached to the outer cell membrane surface to measure the membrane potential. Then, an external voltage source with reverse polarity whose potential difference is not less than the cell membrane potential is connected to the attached electrodes.

The methods of tumor cell growth inhibition disclosed in Patents RU2270663 and RU2253903 are based on the action of the electrical potential on cell membranes from electrodes attached to the tumor. These methods are complicated and traumatic. Moreover, only cells directly contacting with the electrode surface are killed. Tumor cells not contacting with the potential electrodes survive.

There is also an electropositive compound against cancer [10] that works on the basis of positively charged molecules F16. An F16 molecule is attracted by negatively charged cancer cell mitochondria and adheres to them. Mitochondria of various cancer cells have higher negative charge. As a result, F16 are accumulated in cancer cell mitochondria, leading to tumor cell death. Electron microscopic studies showed that F16 induces mitochondria swelling, due to which outer cell membranes are damaged and the tumor cell dies.

A disadvantage of this compound is that molecules F16 can accumulate not only in cancer cell mitochondria but also in normal cells that are also negatively charged, which can lead to their death.

As one can see from the above-discussed analogs, metal oxyhydroxides, polymer materials and molecules capable of selectively affect living cells due to electric charge application to biological structures.

These properties are used for microorganism sorption, wound healing, pain syndrome treatment and tumor cell growth inhibition. Today, however, there is a particular demand for materials with higher sorption capacity and higher biological activity which can be achieved by modifying the electrical properties of materials.

DISCLOSURE OF INVENTION

An object of the present invention is a product that presents low-dimensional structures and/or agglomerates of low-dimensional structures, primarily 2D folded structures of various organic and/or inorganic substances, primarily oxyhydroxides of metals chosen from the group consisting of Al, Fe, Mg and Ti or their composites as well as natural (artificial) and/or synthetic polymer materials with a high local electric field strength achieved by giving them a particular geometrical shape and dimensional parameters.

Another object of the invention is to use the said low-dimensional structures and/or their agglomerates as sorbents of biological objects, inorganic colloidal particles and metal ions.

A further object of the invention is to apply the said low-dimensional structures and/or their agglomerates as wound healing and antibacterial agents, therapeutic agents and products on their basis.

Yet a further object is to apply the said low-dimensional structures and/or their agglomerates to inhibit cancer cell proliferation and to use them as components of antitumor agents.

The object is achieved in that the said low-dimensional, primarily 2D folded structures of organic and/or inorganic substances and/or their agglomerates have folds and faces of irregular shape and exhibit a high local strength of the electric field generated by surface charges on the said folds, faces and edges.

Additionally, the low-dimensional, primarily 2D folded structures and/or their agglomerates are formed by oxyhydroxides of metals chosen from the group consisting of Al, Fe, Mg and Ti or their composites that consist of at least two oxyhydroxides of metals chosen from the said group.

Additionally, the object is achieved in that the low-dimensional, primarily 2D folded structures and/or their agglomerates are made of natural (artificial) polymers, preferably from water insoluble polysaccharides chosen from the group consisting of chitin, chitosan, cellulose and other.

Additionally, the object is achieved in that the low-dimensional, primarily 2D folded structures and/or their agglomerates are made of synthetic polymer materials, preferably from nonpolar polymers (monoelectrets) with a specific conductivity of no more than $10^{-10}$ $Ohm^{-1}$ $cm^{-1}$ chosen from the group consisting of polymers based on vinylidene fluorides, tetrafluoroethylene-hexafluoropropylene (TFE/HFP) copolymer, polypropylene, polyethylene and other.

Additionally, the present invention is a composite of at least one oxyhydroxide of a metal chosen from the group consisting of Al, Fe, Mg and Ti and of at least one artificial polymer material chosen from the group consisting of chitin, chitosan and cellulose.

Additionally, the present invention is a composite of at least one oxyhydroxide of a metal chosen from the group consisting of Al, Fe, Mg and Ti and of at least one synthetic polymer material, preferably nonpolar polymers (monoelectrets) with a specific conductivity of no more than $10^{-10}$ $Ohm^{-1}$ $cm^{-1}$ chosen from the group consisting of polymers based on vinylidene fluorides, tetrafluoroethylene-hexafluoropropylene (TFE/HFP) copolymer, polypropylene, polyethylene and other.

Additionally, the said low-dimensional structures have folds and faces of irregular shape with one dimension ranging from 200 to 500 nm and with at least one dimension, preferably transverse dimension (thickness) of an edge of no more than 10 nm.

It is preferable that the transverse dimension (thickness) of an edge is in the range from 5 to 8 nm, more preferably no more than 2 nm.

Agglomerates consist of alternating, overlapping, conjugated, homogeneously or heterogeneously mixed fragments of 2D structures.

Additionally, the local electric field strength, particularly on folds and faces that form the low-dimensional folded structures, is no less than $10^6$ V/m.

Additionally, the said agglomerates of low-dimensional folded structures are close to spherical shape.

Another object of the invention is achieved by that the said low-dimensional structures and/or their agglomerates are used as sorbents of organic particles (molecules, bacteria, viruses, proteins, antigens, endotoxins) and inorganic particles (metal ions, colloids).

It is preferable that the low-dimensional structures and/or their agglomerates for the said adsorption are used in an aqueous medium, with the pH values of the said medium ranging from 5.0 to 9.5, more preferably 6 to 8.

The further object of the invention is achieved by that the said low-dimensional structures and/or their agglomerates are used as agents that have wound healing and antibacterial activity.

Yet the further object is achieved by that the said low-dimensional structures and/or their agglomerates are used to inhibit tumor cell proliferation.

The said low-dimensional structures and/or their agglomerates are used either alone or if applied onto a carrier material chosen from the group consisting of nonwoven fabrics, fibers, granules, sponges and other porous materials and media, or as components of a composite consisting of the said low-dimensional structures and/or their agglomerates and substances that have pharmacological activity and/or sorption properties.

The property such as high local electric field strength inherent in the said low-dimensional metal oxyhydroxide structures and/or their agglomerates is provided by:

surface charge inherent in oxyhydroxides of metals from the group of Al, Fe, Mg and Ti in aqueous media, and low dimensionality and folds of 2D metal oxyhydroxide structures and their agglomerates due to a small thickness or curvature radius of edges and folds of electrically charged surfaces of the agglomerate elements.

Agglomerates in the present invention should be taken to mean alternating; overlapping; conjugated; homogeneously or heterogeneously mixed 2D structures or their fragments.

Metal oxides and oxyhydroxides as used herein should be taken to mean chemical compounds of the general formula AlOOH, $Al_2O_3 \times nH_2O$, where n=0.8-3, FeOOH, $Fe_2O_3$, $Fe_3O_4$, $TiO_2$, $Mg(OH)_2$ and MgO.

It is known that surface charge density δ for a charged body is proportional to surface curvature k, δ~k, where k~1/r (r is the curvature radius) [11]. Correspondingly, the maximum charge density is observed on edges and folds of the claimed low-dimensional folded structures that form agglomerates/aggregates and have the maximum value of k. A low surface curvature radius of electrically charged metal oxyhydroxide edges and folds gives rise to a strongly inhomogeneous electric field that exerts force F on opposite-sign charged particles.

The inhomogeneous electric field with high local strength on folds and edges of low-dimensional folded structures causes charged particles to move towards increasing electric field strength. The force acting between the charge $q_1$ on the faces, edges and folds of an agglomerate and charge $q_2$ of a sorbate particle is determined by the Coulomb law:

$$F = \frac{q_1 q_2}{4\pi\varepsilon_0 x^2},$$

where x is the distance between sorbent and sorbate.

With regard to the calculated face thickness of low-dimensional folded structures, the electric field strength of an face can be estimated.

The electric field strength (mV/nm) is $$E = \frac{\varphi}{R},$$

where φ is the agglomerate potential, and R is the face thickness.

The force acting on a charged particle in the vicinity of low-dimensional structures is defined by the expression F=qE, where q is the particle charge [11].

The authors calculated (see Examples) that the electric field strength of nonporous particles of regular spherical shape is by about 3 orders of magnitude lower than on the edge of a folded structure.

Correspondingly, at q=const the force acting on a particle (low-dimensional structures and their agglomerates) would be 600 times higher than for compact nonporous spherical particles of the same size.

A similar effect is observed in natural, artificial and synthetic nonpolar polymer materials with a specific conductivity of no more than $10^{-10}$ $Ohm^{-1}$ $cm^{-1}$ because these polymers can acquire an electric charge under an external electric field, friction, electron beam irradiation, corona discharge treatment and other conditions [12]. In this case, high local electric field strength would be achieved on edges and folds of the low-dimensional polymer structures and their agglomerates.

For example, low-dimensional structures and their agglomerates with folded shape and distance up to 50 nm between low-dimensional structures in an agglomerate (FIG. 1) are able to sorb 50 nm sized organic molecules, ions, microbes and viruses, which are trapped by the electric field generated on faces and folds.

The above effect is also demonstrated in FIGS. 5 and 6. It is seen from the figures that disperse particles such as latex spheres (FIG. 5) and colloid silver particles (FIG. 6) adsorb to faces and penetrate into an agglomerate of low-dimensional structures. Thus, the agglomerates formed by the claimed low-dimensional structures exhibit high sorption efficiency.

According to different authors (e.g., Marino et al. [13], Steve Haltiwanger [14]), the electrical potential of normal cells is −60 mV to −100 mV, and the potential of tumor cells is approximately equal to −15 mV to −20 mV. When normal cells start to divide, their electrical potential decreases down to about −15 mV. After the division stops, the cell membrane potential returns back to normal. It is generally agreed that an essential component of cancer treatment would be the restoration of the normal membrane potential and, as a result, normal metabolism of cells. Thus, the regulation of the cell membrane potential is one of the ways to control the functional state of cells.

Positively charged folded structures interacting with negatively charged cell membranes would adhere to the cell surface. The negative charge of the cell membrane would be compensated by the positive charge of the folded structures. The cell membrane potential would increase due to the influence of the electropositive low-dimensional folded structures. On the one hand, this would lead to active division of normal cells and accelerated wound healing and, on the other hand, to inhibition of cancer cell growth.

DETAILED DESCRIPTION OF THE PREFERRED EMBODIMENTS

Example 1. Synthesis of Agglomerates of Electropositive Aluminum Oxyhydroxide (AlOOH) Low-Dimensional Folded Structures Agglomerates with the claimed shape and characteristics were synthesized in a reaction of interaction between water and starting material that was Al/AlN powder produced by electrical explosion of aluminum wire in nitrogen atmosphere, with particle size 80-100 nm, specific surface area 21 $m^2/g$ and MN phase content 70 mass %.

The reaction was conducted in the following way. 100 g of powder were mixed with 10 L of water, and aluminum oxide nanoparticles with an average size of 70 nm were added to the mixture in an amount of 0.1 mass % with respect to the powder mass. The nanoparticles acted as seeds to increase the nucleation rate of transformation products on the seed particles and their crystallization rate. The resulting suspension was heated in the range from 25° C. to 60° C. with vigorous agitation at a rate of 200 rpm using a mechanical mixer.

The reaction was conducted at pH=9.4 for 60 min to achieve a constant pH value.

The obtained product was dried to a constant mass at temperature 90° C. for 4 hours.

The mass of the obtained product was 150 g. The specific surface area of the product measured on a Sorbtometr-M analyzer was 330 $m^2/g$. X-ray diffraction analysis on a DRON-7 diffractometer showed that the obtained product was Al00H.

Figure 1:
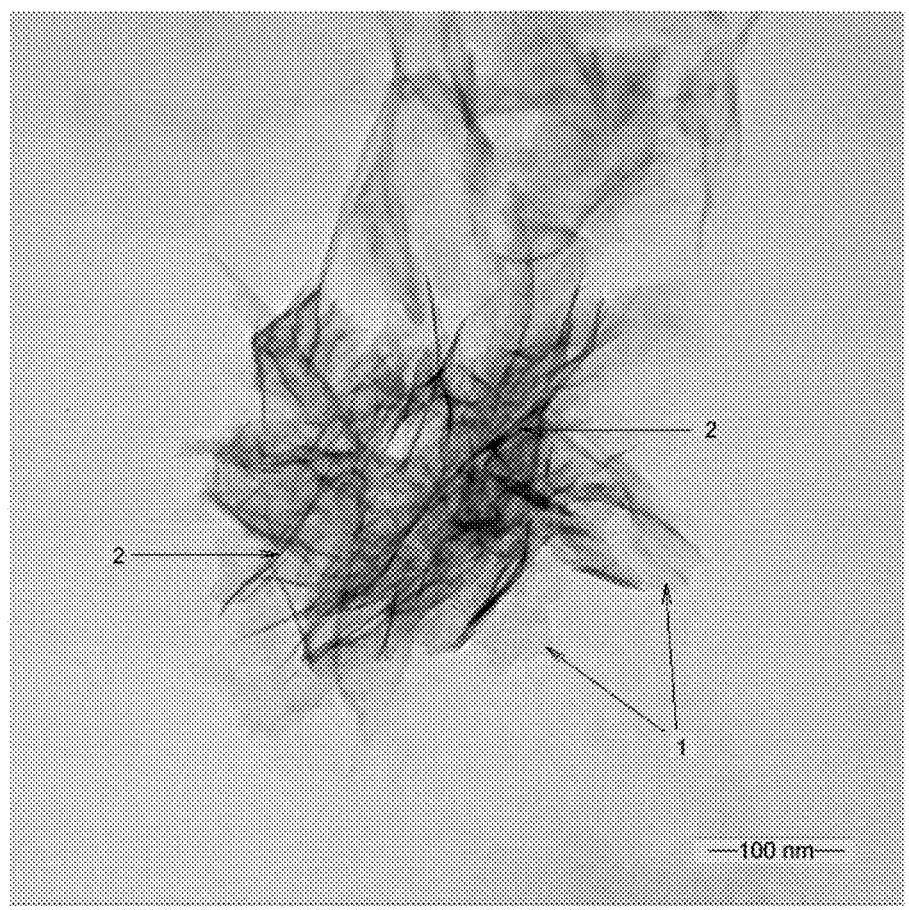
FIG. 1 is a TEM image of aluminum oxyhydroxide agglomerate with the claimed folded structure. Edges (1) and folds (2) are shown.

FIG. 1 depicts a micrograph of agglomerates of oxyhydroxide aluminum low-dimensional folded structures obtained using a JEM-2100 transmission electron microscope. The micrograph demonstrates faces and folds.

Figure 2:
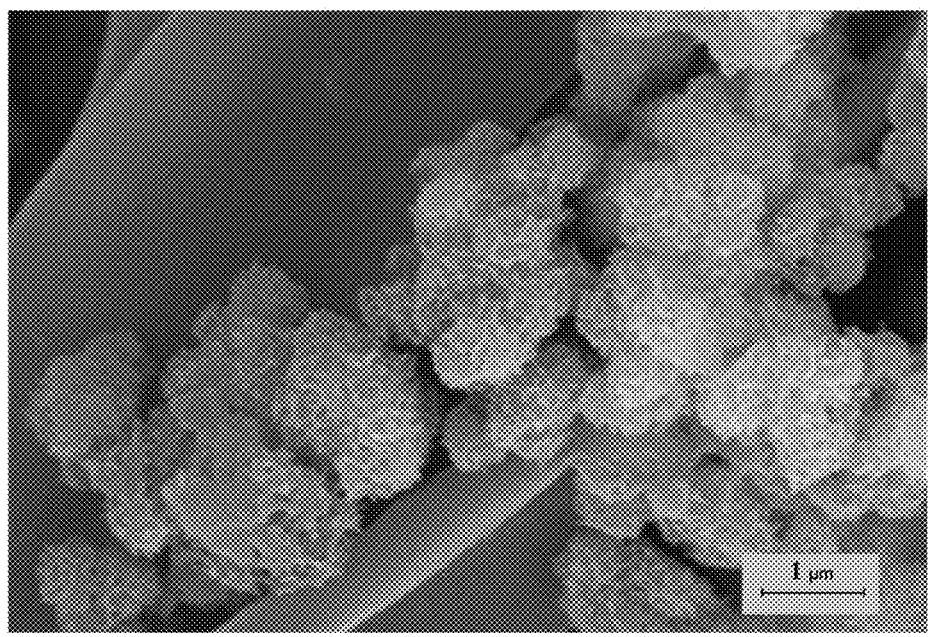
FIG. 2 is a SEM image of aluminum oxyhydroxide agglomerates with the claimed folded structure.

FIG. 2 illustrates a micrograph of agglomerates of low-dimensional folded structures obtained using a LEO EVO 50 scanning electron microscope.

The agglomerate size was in the range from 0.5 μm to 7 μm.

The zeta potential of agglomerates determined with a ZetaSizer Nano ZS was 60 mV. Taking into account the average face thickness of 5 nm, the electric field strength on the edge can be estimated. The electric field strength is $$E = \frac{\varphi}{R},$$

where φ is the agglomerate potential, and R is the face thickness.

The electric field strength on the edge is E=12 mV/nm or $1.2 \cdot 10^7$ V/m. The electric field strength on the surface of a nonporous spherical oxyhydroxide aluminum particle of size 3 μm would be 20 mV/μm or $2 \cdot 10^4$ V/m, i.e. by approximately 3 orders of magnitude lower than on the edge.

The force acting on a charged particle near an agglomerate is determined by the expression F=qE, where q is the particle charge [Savelyev I. V., Physics, a General Course, Moscow: Mir, 1981.].

Correspondingly, at q=const the force acting on a particle for an agglomerate of low-dimensional structures would be 600 times higher than for a nonporous spherical particle of the same size and chemical composition.

Example 2. Synthesis of Agglomerates of Iron Oxyhydroxide (FeOOH) Low-Dimensional Folded Structures Bimetal Fe—Al nanopowder with the particle size of about 100 nm was produced by simultaneous electrical explosion of iron and aluminum wires in nitrogen atmosphere at the ratio of Fe:Al=90:10 mass %. 20 g of powder were mixed with 2000 mL of distilled water, and the mixture was heated up to 60° C. with constant agitation. The pH of the reaction medium was controlled and adjusted to 9.0 using ammonia solution. The reaction was conducted for 60 min. Then, the suspension was filtered, rinsed to neutral pH with distilled water and dried at temperature 90° C. for 4 hours.

The mass of the obtained product was 25.4 g. The specific surface area of the product measured on a Sorbtometr-M analyzer was 220 $m^2/g$. X-ray diffraction analysis on a DRON-7 diffractometer revealed that the product contained primarily goethite FeOOH and a low content of boehmite AlOOH.

Figure 3:
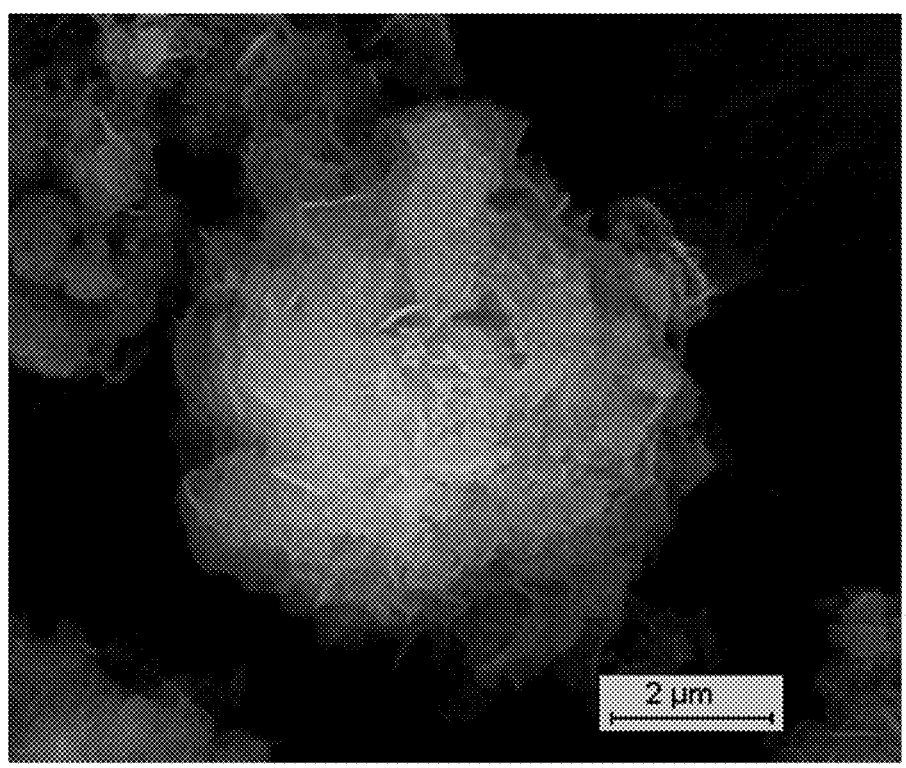
FIG. 3 is a SEM image of iron oxyhydroxide agglomerates with folded structure.

FIG. 3 illustrates a micrograph of a FeOOH/AlOOH composite agglomerate obtained using a LEO EVO 50 scanning electron microscope. The micrograph demonstrates that the agglomerates consist of a great number of low-dimensional folded structures. The properties of the aforesaid composite mainly depend on the morphology and properties of goethite.

The agglomerate size was in the range from 1.0 μm to 12.0 μm. The zeta potential of agglomerates determined with a ZetaSizer Nano ZS was about 50 mV.

The subsequent calculations were similar to those carried out in Example 1. The electric field strength on the edge was $E=2.5 \cdot 10^7$ V/m. For comparison, the electric field strength on the surface of a nonporous spherical particle of size 1 μm with the same chemical composition was $E=5 \cdot 10^4$ V/m.

Example 3. Synthesis of Agglomerates of Ti Oxide Low-Dimensional Folded Structures Agglomerates of Ti oxide low-dimensional folded structures were produced by hydrothermal synthesis at temperature 130° C. for 12 hours in the following way. 100 g of titanium butylate were mixed with 30 mL of acetylacetone and 10 mL of distilled water with constant agitation. Then, 10 mL of concentrated ammonia solution was added to the mixture. The mixture was heated up to 130° C. and hydrothermally treated for 12 hours with constant agitation. The obtained suspension was filtered and rinsed with isopropyl alcohol and distilled water. The washed powder was air dried at temperature 105° C. for 10 hours.

The resulting product was 18 g of titanium oxide low-dimensional folded structures. The specific surface area measured similarly to Examples 1 and 2 was equal to 380 $m^2/g$.

Figure 4:
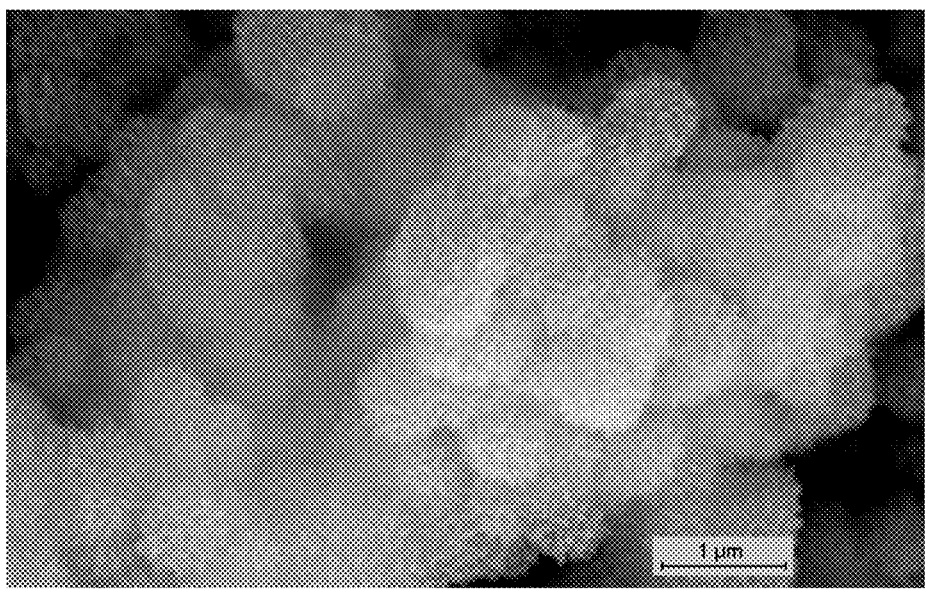
FIG. 4 is a SEM image of titanium oxyhydroxide agglomerates with folded structure.
Figure 5:
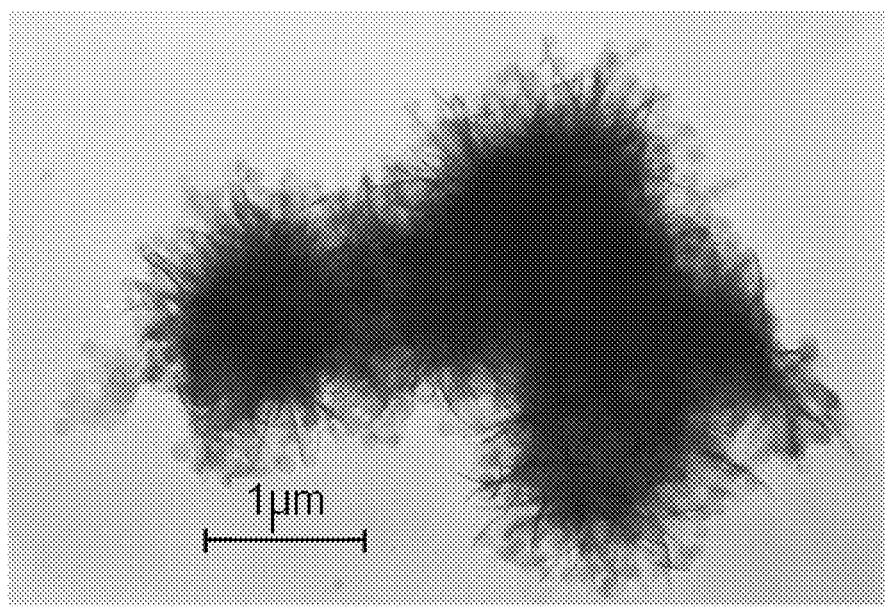
FIG. 5 is a TEM image of agglomerates of folded structures with latex spheres on edges and between folds of aluminum oxyhydroxide agglomerate.
Figure 6:
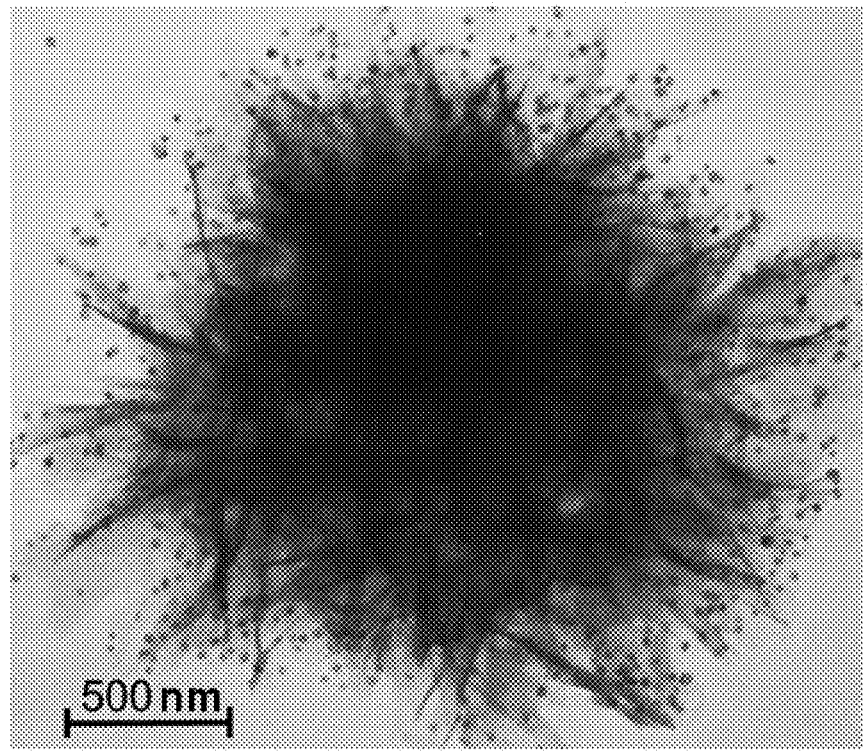
FIG. 6 is a TEM image of agglomerates of folded structures with colloidal silver particles on edges and between folds of aluminum oxyhydroxide agglomerate.

FIG. 4 gives a micrograph of titanium oxide agglomerates obtained on a LEO EVO 50 scanning electron microscope. The micrograph demonstrates that the agglomerates consist of a great number of low-dimensional folded structures.

The agglomerate size was in the range from 0.3 μm to 5.0 μm.

The zeta potential of agglomerates determined with a ZetaSizer Nano ZS was about 40 mV.

The subsequent calculations were similar to those conducted in Example 1. The electric field strength on the edge was $E=1.3 \cdot 10^7$ V/m. For comparison, the electric field strength on the surface of a nonporous spherical particle of size 0.3 μm $E=1.3 \cdot 10^5$ V/m.

Example 4. Synthesis of Polyvinyl Chloride Low-Dimensional Structures

Polyvinyl chloride granules of size no more than 1 mm were dissolved in tetrahydrofuran in a wt % ratio of 10:90, respectively. The suspension was kept for 8 days with periodic agitation. The dissolution of polyvinyl chloride in tetrahydrofuran gave a viscous colorless liquid. 10 mL of polyvinyl chloride/tetrahydrofuran solution were mixed with 5 mg of porous AlOOH synthesized according to Example 1. The prepared mixture was kept for 72 hours with periodic agitation. The supernatant was removed, and the precipitate was mixed with 30 mL of methanol and left for 1 hour for complete sedimentation. The mixture was filtered through filter paper and the sediment was dried in an oven at 30° C. for 24 hours. The resulting dry powder was mixed with 50% NaOOH solution and kept for 5 days under visual control to complete dissolution of AlOOH and sedimentation of polyvinyl chloride low-dimensional structures. The sediment was rinsed with a large volume of ethyl alcohol and dried at 30° C. for 24 hours.

Figure 10:
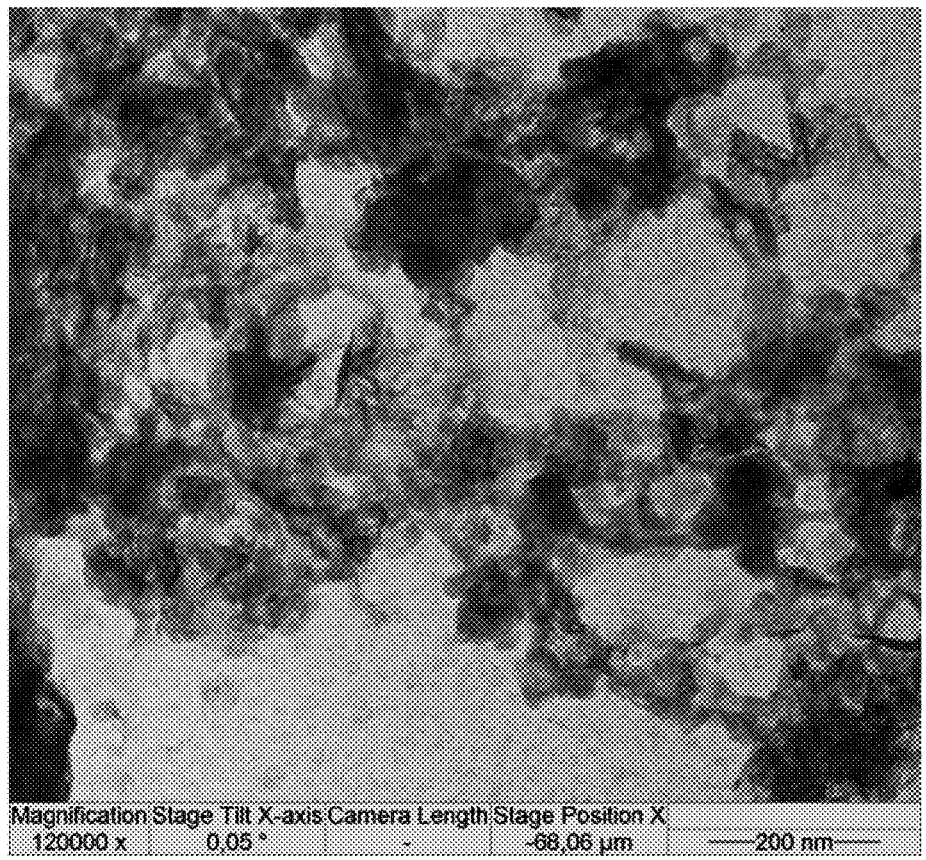
FIG. 10 is a TEM image of polyvinyl chloride low-dimensional folded structures (nanosheets).

FIG. 10 illustrates a micrograph of polyvinyl chloride low-dimensional structures obtained using a JEM 2100 transmission electron microscope. The micrograph shows that the examined sample consists of overlapping polymer plates.

Example 5. Microorganism Adsorption on Metal Oxyhydroxides

*E. coli* 7935, *St. aureus* 209 and *P. aeruginosa* 27583 strains were cultivated on meat peptone agar for 24 hours in a thermostat at temperature 37±1° C. and then a microorganism suspension of $1.0 \times 10^3$ CFU/mL was prepared. *E. coli* 7935 are short (1-3 μm long and 0.5-0.8 μm wide) polymorphic motile and nonmotile gram-negative rods. *St. aureus* 209 are gram-positive spherical cells of diameter 0.5-1.5 μm. *P. aeruginosa* 27583 are gram-negative straight rods of length 1-3 μm and width 0.5-0.7 μm.

The sorption efficiency was measured for *E. coli, St. aureus* and *P. aeruginosa* bacteria according to the recommendations by Voroshilova et al. [Voroshilova A. A. and Dianova E. D., Oil-Oxidizing Bacteria as Markers of Biological Oil Oxidation Intensity under Natural Conditions, Microbiologiya, 1952, vol. 21, no. 4, p. 408-415.]. To determine the sorption efficiency, autoclaved samples of mass 100 mg were introduced into sterile flasks and mixed with 30 mL of bacterial suspension with concentration $1.0 \times 10^3$ CFU/mL. Microorganism adsorption on the samples occurred with constant agitation of suspension for 30 min using a magnet mixer at a rate of 500 rpm. The samples were then centrifuged for 3 min at 1300 rpm, and 1 mL of supernatant was inoculated onto meat peptone agar plates that were incubated in a thermostat at 37±1° C. for 24 h. Colonies were counted after 24 hours of incubation.

The sorption efficiency values are given in Table 1.

TABLE 1

Microorganism sorption efficiency

| | Sorption efficiency | | |
|---|---|---|---|
| Product | *E. coli* | *St. aureus* | *P. aeruginosa* |
| Al oxyhydroxide | 99.8 ± 0.24 (n = 11) | 93.7 ± 0.22 (n = 6) | 96.5 ± 0.39 (n = 14) |
| Fe oxyhydroxide | 92.1 ± 0.20 (n = 10) | 95.5 ± 0.25 (n = 10) | 87.3 ± 0.40 (n = 10) |
| Ti oxide | 89.0 ± 0.25 (n = 11) | 96.3 ± 0.20 (n = 8) | 87.3 ± 0.30 (n = 10) |

Experiments on microorganism sorption depending on pH were conducted in a similar way (Table 2).

TABLE 2

Microorganism sorption efficiency of Al oxyhydroxide depending on pH

| Initial *E. coli* concentration, CFU/mL | Suspension pH before decontamination | *E. coli* supernatant concentration, CFU/mL | Adsorbed cells, % |
|---|---|---|---|
| $3.00 \cdot 10^3$ | 5.0 | $<1 \cdot 10^2$ | >99.99 |
| $2.80 \cdot 10^3$ | 7.0 | $1.6 \cdot 10^3$ | >99.94 |
| $2.50 \cdot 10^3$ | 9.0 | $<1 \cdot 10^2$ | >99.99 |

Example 6. Adsorption of Inorganic Ions on Iron Oxyhydroxide with the Claimed Shape and Characteristics A model solution of metals was prepared which contained 0.25 mg/L arsenic in the form of arsenate ions, 0.4 mg/L manganese, 0.5 mg/L lead and 3 mg/L copper. 100 mL of the model solution were mixed with 1 g of agglomerates of iron oxyhydroxide folded structures, and the obtained mixture was agitated for 1 hour at room temperature. The concentration of metal ions was determined after sorption. The results are given in Table 3.

TABLE 3

Residual concentration of inorganic impurities in water

| | Element content, mg/L | | MPC for drinking water, mg/L |
|---|---|---|---|
| Element | Before cleaning | After cleaning | |
| Arsenic | 0.25 ± 0.02 | 0.037 ± 0.004 | 0.05 |
| Manganese | 0.40 ± 0.05 | 0.06 ± 0.01 | 0.1 |
| Lead | 0.50 ± 0.03 | 0.18 ± 0.03 | 0.3 |
| Copper | 3.0 ± 0.2 | 0.55 ± 0.04 | 1.0 |

The residual concentration of inorganic impurities after inorganic ion adsorption on iron oxyhydroxide folded structures in water under static conditions was lower than the MPC for drinking water [SanPiN 2.1.4.1074-01 Drinking Water. Hygienic Requirements on Water Quality in Drinking Water Supply Systems. Quality Control.].

Example 7. Application of Metal Oxides/Oxyhydroxides with the Claimed Shape and Characteristics for Wound Healing Experiments were performed on white outbred male rats weighing 140-210 g, 100 animals in total: 20 animals in each trial (4 hydroxide types) and 20 untreated control group animals. The animals were shaved in the dorsal region, and a skin region of 2 cm$^2$ was marked. A piece of skin and subcutaneous tissue were excised in the marked region to an underneath fascia. A Kocher clamp on the wound edges and bottom was used to create tissue injury.

The wound was contaminated with a St. aureus suspension of 5·10$^5$ CFU/mL (An Infected Soft Tissue Wound Model/Sukhovey Yu. G., Tsiryatyeva S. B., Minin A. S., Samusev R. S., Sych A. S., Kostolomova E. G.//RF Patent No. 2321898, 10 Apr. 2008, publ. in Bullet. No. 1). The infecting dose was 2 mL per 200 g of rat weight. The infected wound was secured with Teflon rings with covers to prevent disturbance of the wound by grooming The animals were operated under ether narcosis in non-sterile conditions. Wound treatment began 48 hours after operation when the wound demonstrated acute suppurative inflammation. Metal oxyhydroxides produced by Examples 1-3 were applied to the wound as dry powder of mass 2 g once a day. The treatment was continued depending on the wound healing rate.

The development of the purulent process in the wound was assessed by daily observations of the animal for 25 days.

The following parameters were evaluated:
purulent or serous wound exudate;
local inflammatory reaction (hyperemia and edema in the wound region);
rate of wound cleaning (removal of necrotic tissue and elimination of wound discharge);
rate of secondary scar formation.

The wound healing criteria were the time of removal of purulent and necrotic tissue from the wound, granulation tissue formation, beginning and completion of wound epithelization. Wound healing outcomes were also assessed. The data are given in Table 4.

The animals were treated according to Order No. 267 of Jun. 19, 2003 on Good Laboratory Practice Guidelines and according to the rules adopted by the European Convention for the Protection of Vertebrate Animals used for Experimental and other Scientific Purposes (Strasbourg, 1986). Experimental animals were kept in standard vivarium plastic animal cages, one per cage, on wood shavings bedding, with free access to food and water (standard mouse diet), under a natural light regime.

Example 8. Application of Aluminum Oxyhydroxide with the Claimed Shape and Characteristics for the Inhibition of Cancer Cell Growth Experiments were conducted on the established HOS (TE85, clone F5) cell line from human osteosarcoma. The cells were plated in 50 mL culture flasks at a cell density of 1.1 mln per flask. A monolayer was formed during 2-3 days. The formed monolayer was rinsed with a cell culture medium without serum. 0.005, 0.01 and 0.03 g of aluminum oxyhydroxide powder was suspended in 2 mL of the cell culture medium and applied to the cell monolayer. Then, 5 mL of cell culture medium containing 2% fetal bovine serum was added. The cells were incubated in a thermostat at 37±1° C. according to the recommendations for this cell line. To determine the proliferation index (PI, ratio of the number of newly proliferated cells to the number of parent cells) the cell monolayer was detached by trypsin and versene after 24, 48 and 72 hours of contact with aluminum oxyhydroxide powder. Cells were counted on a hemocytometer (Goryaev chamber) by using trypan blue vital staining to determine the number of living and dead cells. In trypan blue staining living cells remain colorless, while dead cells are colored blue. All experiments were performed with control in 2 replicates, and cells were counted in 3 replicates.

The proliferation index was determined taking into account the inoculated dose per 1 culture flask. It was equal to 1.1 mln in all experiments, and the volume of the medium for cell detachment and resuspension was 3.0 mL.

According to the purpose of the experiment, HOS cells were grown as a monolayer that was treated with increasing aluminum oxyhydroxide fractions of 0.005, 0.01 and 0.03 g.

TABLE 4

Results of skin wound decontamination and healing in animal groups*

| Group No. | Visible wound cleaning, days | Visible granulation, days | Initiation of visible (edge) epithelization, days | 50% visible epithelization, days | Completion of epithelization, days |
|---|---|---|---|---|---|
| Control | 14.5 ± 1.7 | 12.5 ± 1.3 | 11.5 ± 1.0 | 18.0 ± 2.5 | 21.0 ± 2.6 |
| Al oxy-hydroxide | 3.0 ± 0.3 | 2.5 ± 0.3 | 2.0 ± 0.2 | 4.4 ± 0.4 | 8.5 ± 0.9 |
| Fe oxy-hydroxide | 3.5 ± 0.3 | 2.0 ± 0.2 | 2.0 ± 0.2 | 5.0 ± 0.5 | 8.0 ± 0.5 |
| Ti oxide | 4.5 ± 0.4 | 5.5 ± 0.5 | 3.5 ± 0.5 | 4.0 ± 0.4 | 9.5 ± 1.0 |

*$p < 0.05$

The given data indicate that the application of metal oxyhydroxides accelerated significantly wound healing with respect to the control group animals. The complete epithelization time reduced by 40-62% with respect to the control untreated group. This effect is evidently related both to wound decontamination and to tissue cell proliferation (epithelization). It is noticeable that wound healing occurred without formation of rough scars.

The proliferation of HELA (human cervical carcinoma), MCF-7 (human breast cancer) and UM-SCC-14C (human squamous cell carcinoma of skin) cell lines was determined by inoculating the cells in a 96 well plate (Saphire) at a density of 1×10$^5$ cells/well in the DMEM or MEM cell culture medium containing 2 mM L-glutamine, 100 units penicillin, 100 μg/mL streptomycin and 10% fetal bovine serum. Aluminum oxyhydroxide powder was suspended in a phosphate buffer (pH 7.4) at a concentration of 0.005 g/mL and applied to the cell monolayer. The control group was not treated by aluminum oxyhydroxide. The cells were incubated for 24 and 48 hours in a thermostat at 37±1° C. in a 5% humid $CO_2$ atmosphere. The cell proliferation was detected by incorporating 5-bromo-2'-deoxyuridine (BrdU) into the newly synthesized DNA of replicating cells (synthetic phase of the cell cycle) with the replacement of thymidine during DNA replication. The fluorescent detection of BrdU was carried out using a Tecan microplate reader (Austria) with excitation wave length at 370 nm and emission wavelength at 470 nm.

The influence of aluminum oxyhydroxide on tumor cell vitality for HELA (human cervical carcinoma), MCF-7 (human breast cancer) and UM-SCC-14C (human squamous cell carcinoma of skin) cell lines was studied by inoculating the cells in 15-cm cell culture dishes and cultivating them in the DMEM or MEM cell culture medium containing 2 mM L-glutamine, 100 units penicillin, 100 µg/mL streptomycin and 10% fetal bovine serum until a confluent monolayer was formed. Aluminum oxyhydroxide powder was suspended in a phosphate buffer (pH 7.4) at a concentration of 0.005 g/mL and transferred applied to cell monolayer. The cells were incubated for 24 and 48 hours in a thermostat at 37±1° C. in a 5% humid $CO_2$ atmosphere. To determine the number of living cells, the monolayer was detached with a TrypLE Select solution (Gibco) and cells in the obtained suspension were counted using a hemocytometer (Goryaev chamber). The number of living and dead cells was determined by using 0.1% trypan blue vital staining.

Figure 7:
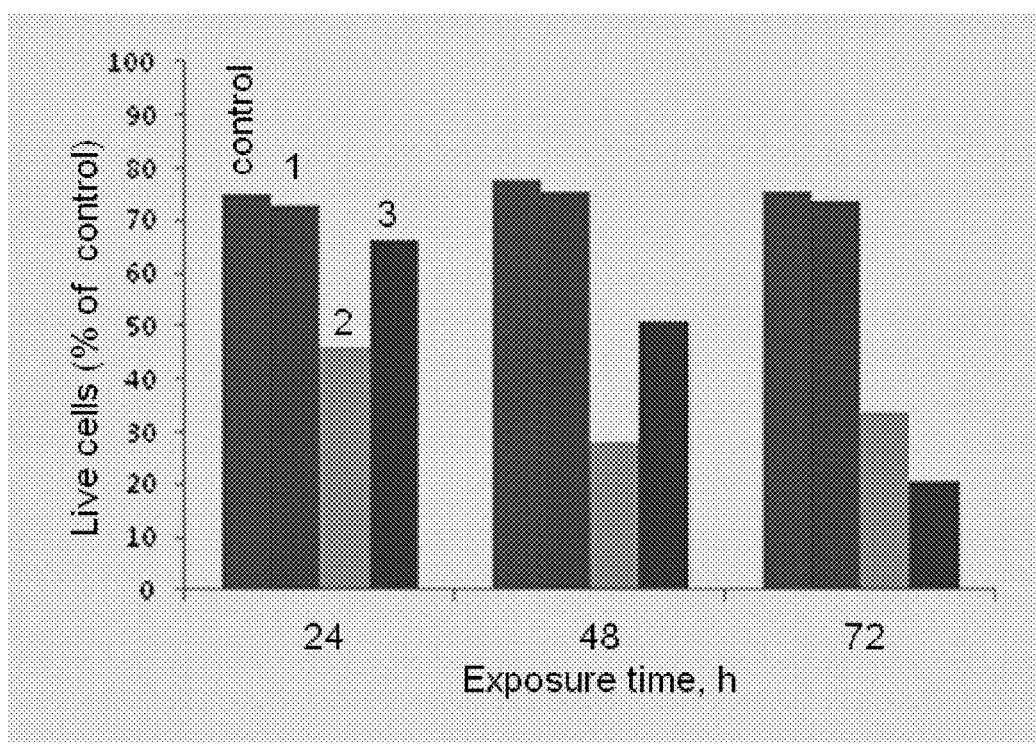
FIG. 7 are results of experiments on HOS cells: number of living HOS cells (%) depending on aluminum oxyhydroxide content in 2 ml of cell culture medium: 1—0.005 g, 2—0.01 g, 3—0.03 g FIG. 8 are results on HELA, MCF-7 and UM-SCC-14C cells: number of living cancer cells (%) in 24 (a) and 48 hours (b).
Figure 8:
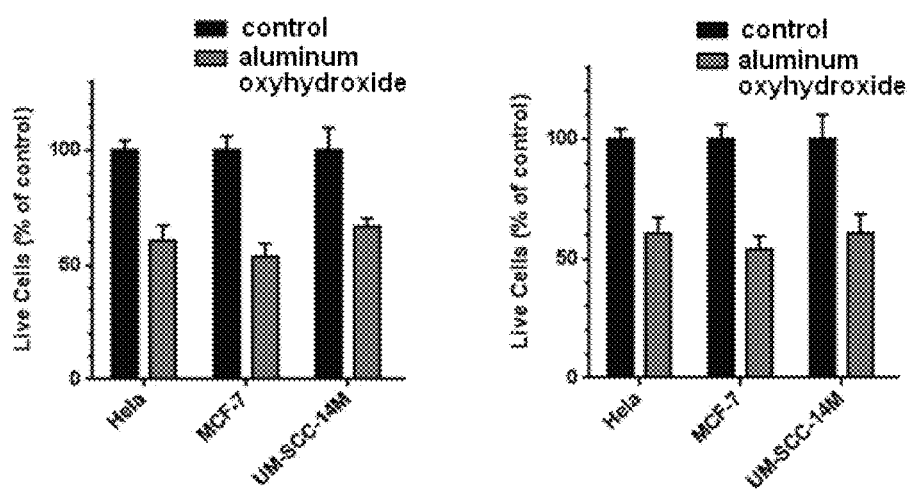
Figure 9:
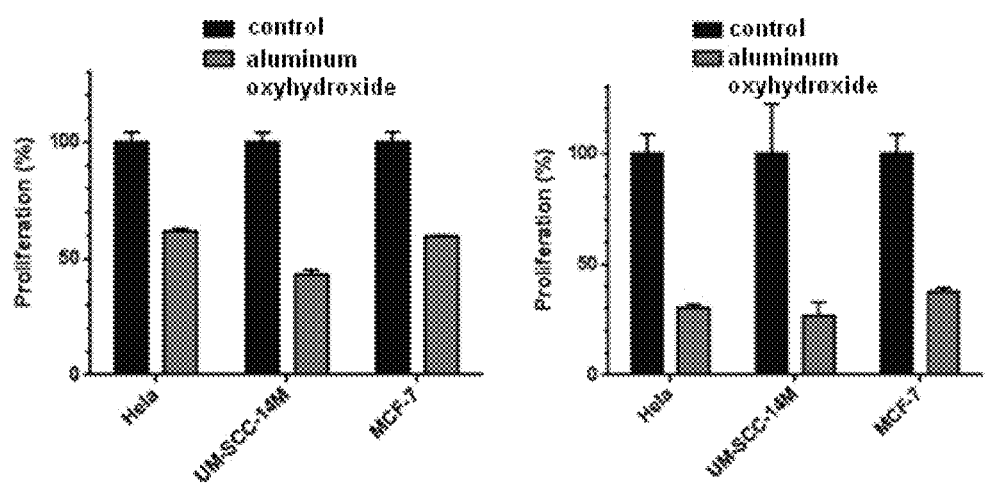
FIG. 9 are results on HELA, MCF-7 and UM-SCC-14C cells: cancer cell proliferation (%) in 24 (a) and 48 hours (b).

Before experiments aluminum oxyhydroxide powder samples were steam sterilized three times in 24 hour intervals at 121° C. for 20 min The results of experiments on HOS cells are displayed in FIG. 7. It shows the dependence of the number of living HOS cells (%) on the aluminum oxyhydroxide content in 2 ml of cell culture medium: 1—0.005 g, 2—0.01 g, 3—0.03 g, and in Table 5 (W is the percentage of cells). The experimental results for HELA, MCF-7 and UM-SCC-14C cell lines are given in FIGS. 8 and 9. FIG. 8 demonstrates the number of living cancer cells (%) in 24 (a) and 48 hours (b). FIG. 9 demonstrates the results of cancer cell proliferation (%) in 24 (a) and 48 hours (b).

It follows from the given data that aluminum oxyhydroxide applied to tumor cell cultures significantly inhibits cell proliferation. Aluminum oxyhydroxide can be used as powder or if applied onto a fibrous or porous carrier.

Example 9. Microorganism Adsorption on Polyvinyl Chloride Low-Dimensional Structures

*E. coli* 7935 cultures were cultivated on meat peptone agar for 24 hours in a thermostat at 37±1° C. and then a microorganism suspension $1.0 \times 10^3$ CFU/mL was prepared.

The sorption efficiency was assessed using *E. coli* bacteria following the recommendations by Voroshilova et al. [Voroshilova A. A. and Dianova E. D., Oil-Oxidizing Bacteria as Markers of Biological Oil Oxidation Intensity under Natural Conditions, Microbiologiya, 1952, vol. 21, no. 4, p. 408-415.]. To determine the sorption efficiency, autoclaved samples of mass 10 mg were introduced into sterile flasks and mixed with 3 mL of bacterial suspension with concentration $1.0 \times 10^3$ CFU/mL. Microorganism adsorption on the samples occurred with constant agitation of suspension for 30 min using a magnet mixer at a rate of 500 rpm. The samples were then centrifuged for 3 min at 1300 rpm, and 1 mL of supernatant was inoculated onto meat peptone agar plates that were incubated in a thermostat at 37±1° C. for 24 h. Colonies were counted after 24 hours of incubation.

The sorption efficiency values are given in Table 5.

TABLE 5

Microorganism sorption efficiency of polyvinyl chloride low dimensional structures

| Product | Sorption efficiency *E. coli* |
|---|---|
| Polyvinyl chloride | 94.0 ± 0.35 (n = 14) |

References

1. Reid B., Song B., McCaig C. D., and Zhao M., Wound Healing in Rat Cornea: The Role of Electric Currents, FASEB J., 2005, 19, pp. 379-386.
2. Keese C. R., Wegener J., Walker S. R., and Giaever I., Electrical Wound-Healing Assay for Cells in Vitro, Proc. Natl Acad. Sci. USA, 2004, 101, pp. 1554-1559.
3. Nature Letters, 27 Jul. 2006, vol. 442, pp. 457-460
4. Cone C. D., Unified Theory on the Basic Mechanism of Normal Mitotic Control and Oncogenesis, J Theor. Biol., 971, 30:15U181.
5. Marino A. A., Iliev I. G., Schwalke M. A. et al., Association between Cell Membrane Potential and Breast Cancer, Tumor Biol., 1994, 15:82-89.
6. Binggeli R. and Cameron I. L., Cellular Potentials of Normal and Cancerous Fibroblasts and Hepatocytes, CANCER RESEARCH, June 1980, vol. 40, pp. 1830-1835.
7. Sundelacruz S., Levin, M., and Kaplan, D. L., Role of Membrane Potential in the Regulation of Cell. Proliferation and Differentiation, Stem Cell Rev. and Rep., 2009, 5:231-246
8. Larichev M. N., Shaitura N. S., Kolokolnikov V. N., Laricheva O. O., Shkolnikov E. I., and Artemov V. V., Production of Nonstructured Products in Micron-Sized Aluminum Powder Oxidation by Water in Ultrasonic Field, Perspekt. Mater., 2010, no. 9, pp. 290-294
9. Drobyshev V. A., POLYMEDEL: Medical Application of Polymer Electret Film Polymedel, Novosibirsk: IPK Chuvashiya, 2010, 36 p.
10. Fantin V. R., Berardi M. J., Scorrano L., Korsmeyer S. J., and Leder P. A., Novel Mitochondriotoxic Small Molecule that Selectively Inhibits Tumor Cell Growth, Cancer Cell, 2002, 2: 29-42.
11. Savelyev I. V., Physics, a General Course, Moscow: Mir, 1981.
12. Gorokhovatskii Yu. A., The Electret Effect and Its Application, Soros Educational J., 1997, no. 8, pp. 92-98.
13. Marino A., Iliev I., and Schwalke M., Association between Cell Membrane Potential and Breast Cancer, Tumor Biol., 1994, 15:82-89.
14. Steve Haltiwanger M. D., The Electrical Properties of Cancer Cells, http://www.royalrife.com/haltiwangerl.pdf

What is claimed is:

1. Folded structures and/or their agglomerates, the folded structures and/or their agglomerates comprising folds and faces of an irregular shape, wherein the irregular shape has one of the dimension ranging from 200 to 500 nm and at least one dimension being a thickness of an edge of no more than 10 nm, wherein the agglomerates comprise alternating, overlapping, conjugated, homogeneously or heterogeneously mixed fragments of two-dimensional structures, and the folded structures and/or their agglomerates exhibiting a local strength of an electric field generated by surface charges on the folds, faces and edges, that is no less than $10^6$ V/m, wherein the structures and/or the agglomerates are formed by:
- metal oxyhydroxides or their composites comprising at least two oxyhydroxides of metals selected from the group consisting of Al, Fe, Mg and Ti, or
- natural or artificial polymers selected from the group consisting of chitin, chitosan and cellulose, or synthetic polymer materials, or
- a composite comprising at least one oxyhydroxide of a metal selected from the group consisting of Al, Fe, Mg, and Ti; and at least one natural or artificial polymer material selected from the group consisting of chitin, chitosan and cellulose or at least one synthetic polymer material.

2. The folded structures and/or their agglomerates of claim 1, wherein the synthetic polymer materials are nonpolar polymers, wherein the nonpolar polymers have a specific conductivity of no more than $10^{-10}$ $Ohm^{-1}$ $cm^{-1}$ and are selected from the group consisting of vinylidene fluorides, tetrafluoroethylene-hexafluoropropylene (TFE/HFP) copolymer, polypropylene, polyethylene and polar polymers.

3. The folded structures and/or their agglomerates of claim 2, wherein the nonpolar polymer material is a monoelectret.

4. The folded structures and/or their agglomerates of claim 2, wherein the polar polymer is polyvinyl chloride.

5. The folded structures and/or their agglomerates of claim 1, wherein the thickness of the edge is between 5 and 8 nm.

6. The folded structures and/or their agglomerates of claim 1, wherein the thickness of the edge is no more than 2 nm.

7. Sorbents of particles comprising the structures and/or their agglomerates according to claim 1.

8. The sorbents of claim 7, wherein the pH values range from 6 to 8.

9. The sorbents of particles of claim 7, wherein the organic particles are molecules, bacteria, viruses, proteins, antigens or endotoxins.

10. An agent comprising the folded structures and/or their agglomerates according to claim 1, wherein the agent exhibits wound healing and antibacterial activity.

11. An agent comprising the folded structures and/or their agglomerates according to claim 1, wherein the agent inhibits proliferation of tumor cells.

12. A carrier material comprising folded structures and/or their agglomerates according to claim 1.

13. The carrier material comprising folded structures and/or their agglomerates of claim 12, wherein the carrier material is selected from the group consisting of nonwoven fabrics, fibers, granules, sponges and porous materials.

14. A composition comprising a pharmacologically active substance and the folded structures and/or their agglomerates according to claim 1, wherein the pharmacologically active substance exhibits sorption properties.

* * * * *